(12) United States Patent
Rovegno

(10) Patent No.: US 7,220,226 B2
(45) Date of Patent: May 22, 2007

(54) REMOVABLE OPERATING DEVICE FOR A FLEXIBLE ENDOSCOPIC PROBE FOR MEDICAL PURPOSES

(75) Inventor: Jean Rovegno, La Ciotat (FR)

(73) Assignee: Tokendo (FR)

( * ) Notice: Subject to any disclaimer, the term of this patent is extended or adjusted under 35 U.S.C. 154(b) by 397 days.

(21) Appl. No.: 10/880,186

(22) Filed: Jun. 29, 2004

(65) Prior Publication Data

US 2005/0027165 A1 Feb. 3, 2005

(30) Foreign Application Priority Data

Jul. 4, 2003 (FR) ................................. 03 08223

(51) Int. Cl.
*A61B 1/00* (2006.01)
(52) U.S. Cl. .................. 600/104; 600/153; 600/154; 600/156; 604/533; 604/284
(58) Field of Classification Search ............... 600/104, 600/133, 153–159, 131; 604/533–535, 284
See application file for complete search history.

(56) References Cited

U.S. PATENT DOCUMENTS

| | | | | |
|---|---|---|---|---|
| 3,830,225 A | * | 8/1974 | Shinnick ..................... 600/581 |
| 4,198,958 A | * | 4/1980 | Utsugi ......................... 600/154 |
| 4,361,138 A | * | 11/1982 | Kinoshita ................... 600/159 |
| 4,469,090 A | * | 9/1984 | Konomura .................. 600/159 |
| 4,561,428 A | * | 12/1985 | Konomura .................. 600/159 |
| 4,661,110 A | * | 4/1987 | Fortier et al. ............... 604/256 |
| 4,736,732 A | * | 4/1988 | Shimonaka et al. ......... 600/158 |
| 4,794,913 A | * | 1/1989 | Shimonaka et al. ......... 600/159 |
| 4,968,309 A | * | 11/1990 | Andersson ................... 604/534 |
| 4,972,828 A | * | 11/1990 | Ito .............................. 600/153 |
| 4,994,048 A | * | 2/1991 | Metzger ..................... 604/533 |
| 5,209,219 A | * | 5/1993 | Hollobaugh ................ 600/154 |
| 5,257,773 A | * | 11/1993 | Yoshimoto et al. ......... 251/339 |
| 5,299,561 A | * | 4/1994 | Yoshimoto .................. 600/159 |
| 5,322,263 A | * | 6/1994 | Yoshimoto et al. ......... 251/251 |
| 5,350,356 A | * | 9/1994 | Bales et al. ................... 604/27 |
| 5,354,291 A | * | 10/1994 | Bales et al. .................. 604/35 |
| 5,776,117 A | * | 7/1998 | Haselhorst et al. ......... 604/533 |
| 5,840,015 A | * | 11/1998 | Ogino ........................ 600/159 |
| 5,846,221 A | * | 12/1998 | Snoke et al. ................ 604/500 |

(Continued)

FOREIGN PATENT DOCUMENTS

DE 19721030 12/1998

(Continued)

*Primary Examiner*—John P. Leubecker
*Assistant Examiner*—Victoria W. Chen
(74) *Attorney, Agent, or Firm*—Bachman & LaPointe

(57) ABSTRACT

An operating device is provided which includes an instrument insertion conduit, having a distal end connectable to the operating channel input of a handle of an endoscopic probe, the proximal end of the instrument insertion conduit forming an instrument input for the operating device, a suction assembly comprising a suction conduit communicating with the insertion conduit and a control device for selectively connecting the suction conduit to a pump, to suck out fluids through the operating channel, and a connecting conduit putting the suction conduit into communication with the insertion conduit, and the length of which is such that when the operating device is fixed on the handle, the suction control device is positioned close to the control means located in a proximal part of the handle.

14 Claims, 3 Drawing Sheets

U.S. PATENT DOCUMENTS

| | | | |
|---|---|---|---|
| 5,910,105 A * | 6/1999 | Swain et al. | 600/131 |
| 5,989,240 A * | 11/1999 | Strowe | 604/533 |
| 5,992,899 A * | 11/1999 | Strowe | 285/93 |
| 6,004,263 A * | 12/1999 | Nakaichi et al. | 600/176 |
| 6,053,934 A * | 4/2000 | Andrews et al. | 606/207 |
| 6,083,151 A * | 7/2000 | Renner et al. | 600/114 |
| 6,146,374 A * | 11/2000 | Erskine et al. | 604/533 |
| 6,406,470 B1 * | 6/2002 | Kierce | 604/535 |
| 6,423,053 B1 * | 7/2002 | Lee | 604/533 |
| 6,494,826 B1 * | 12/2002 | Chatenever et al. | 600/112 |
| 6,620,096 B2 * | 9/2003 | Arai et al. | 600/156 |
| 6,652,509 B1 * | 11/2003 | Helgren et al. | 604/535 |
| 6,808,521 B1 * | 10/2004 | McMichael | 604/533 |
| 6,860,516 B2 * | 3/2005 | Ouchi et al. | 285/124.1 |
| 6,869,392 B2 * | 3/2005 | Dickopp et al. | 600/104 |
| 6,869,395 B2 * | 3/2005 | Page et al. | 600/127 |
| 6,875,169 B2 * | 4/2005 | Berci et al. | 600/112 |
| 6,878,106 B1 * | 4/2005 | Herrmann | 600/104 |
| 2002/0188175 A1 * | 12/2002 | Levine et al. | 600/159 |
| 2004/0158203 A1 * | 8/2004 | Cover et al. | 604/118 |
| 2004/0167379 A1 * | 8/2004 | Akiba | 600/154 |
| 2004/0215058 A1 * | 10/2004 | Zirps et al. | 600/127 |
| 2004/0220449 A1 * | 11/2004 | Zirps et al. | 600/104 |
| 2004/0260151 A1 * | 12/2004 | Akiba | 600/159 |
| 2005/0049459 A1 * | 3/2005 | Hern | 600/121 |
| 2005/0119522 A1 * | 6/2005 | Okada | 600/106 |
| 2005/0119525 A1 * | 6/2005 | Takemoto | 600/114 |
| 2005/0124856 A1 * | 6/2005 | Fujikura et al. | 600/115 |
| 2005/0203543 A1 * | 9/2005 | Hilal et al. | 606/108 |
| 2005/0222494 A1 * | 10/2005 | Prescott | 600/113 |
| 2005/0245899 A1 * | 11/2005 | Swisher | 604/533 |
| 2006/0041189 A1 * | 2/2006 | Vancaillie | 600/154 |
| 2006/0116552 A1 * | 6/2006 | Noguchi et al. | 600/159 |
| 2006/0135846 A1 * | 6/2006 | Hunt | 600/104 |

FOREIGN PATENT DOCUMENTS

| | | |
|---|---|---|
| WO | 9325139 | 12/1993 |

* cited by examiner

REMOVABLE OPERATING DEVICE FOR A FLEXIBLE ENDOSCOPIC PROBE FOR MEDICAL PURPOSES

FIELD OF THE INVENTION

This invention relates to the domain of flexible endoscopic probes for medical purposes of the fibrescope or videoendoscope type provided with an operating channel, an instrumentation input and a suction control.

It is particularly applicable to the domain of medical endoscopy, and more particularly to bronchoscopy.

BACKGROUND OF THE INVENTION

"Endoscopy" usually means a visual examination made inside an obscure cavity using an "endoscope", a "fibrescope", or a "videoendoscope".

The term "fibrescope" usually denotes a flexible endoscopic probe that is inserted into an obscure cavity so that a user can firstly observe a target located inside the cavity through a lens, and secondly modify the orientation of the distal end of the probe inside the cavity. To achieve this, a fibrescope naturally integrates an optical device, an illumination device and a mechanical device. The mechanical device of a fibrescope is composed of an articulated distal tip deflection, a control handle and four cables located inside a flexible cylindrical duct connecting the control handle to the articulated distal tip deflection. The fibrescope handle is provided with two manually controlled devices one of which acts on the pair of cables activating the orientation of the tip deflection in one plane, and the other acting on the other pair of cables activating the orientation of the tip deflection in a plane perpendicular to the previous plane. The optical device of a fibrescope is composed of an objective placed in the distal face of an end piece fixed to the distal end of the tip deflection, an optical transport system for the image output by the distal objective, the transport system being composed of a flexible beam of ordered optical fibers passing in sequence through the articulated tip deflection, the flexible duct and then in the handle and connecting the lens to the distal objective, and a lens with a dioptric adjustment fixed to the control handle that the user can use to observe the magnified image of the target located in front of the distal objective of the fibrescope and transmitted through the image optical transport system. The illumination device of a fibrescope is composed of a beam of unordered optical fibers passing in sequence in the articulated tip deflection, in the flexible duct, in the handle, and then in an umbilical cable fixed to the control handle. The distal end of the beam of fibers, housed in the distal face of the end piece fixed to the distal end of the articulated tip deflection, illuminates the observed target when its proximal end housed in an illumination end piece integrated into the connection device forming the proximal end of the umbilical cable, is connected to a light generator. Under these conditions, use of the fibrescope described above requires the joint use of a light generator.

The term "videoendoscope" usually denotes a flexible endoscopic probe that, when inserted in an obscure cavity, enables a user firstly to observe a target on the screen of a video monitor located inside the cavity and secondly to modify the orientation of the distal end of the probe inside the cavity. To achieve this, a videoendoscope naturally comprises an imagery device, an illumination device and a mechanical device. The illumination device and the mechanical device of a videoendoscope are identical to devices of the same nature integrated into a fibrescope and described above, in all respects. The imagery device of a videoendoscope comprises mainly the following elements:

an optoelectronic device housed in the distal end piece fixed to the distal end of the articulated tip deflection and comprising an objective housed in the distal face of said end piece, a color CCD sensor on the photoelectric substrate on which the real image of the observed target output by the objective is formed, and an interface microcircuit designed to correct electrical signals received or generated by the CCD sensor;

a multiconductor electrical cable routed in sequence through the articulated tip deflection, the flexible duct, the control handle and then the umbilical cable fixed to the control handle, the distal end of said cable being electrically fixed to the interface microcircuit of the distal optoelectronic device, while its proximal end is electrically fixed to a multipin connection socket integrated into the connection device forming the proximal end of the umbilical cable;

a video processor for synchronization of the electrical power supply of the distal optoelectronic device, processing of the electrical signal generated by the optoelectronic device, and outputting a video signal that is directly useable on a color monitor; the video processor with a panel of control keys enables the user to adjust the video image parameters, a video output connector that will be connected to a video monitor, and a multipin connector that will be connected to a multipin connection socket integrated into the connection device forming the proximal end of the umbilical cable of the videoendoscope.

Under these conditions, operation of the videoendoscope described above requires joint use of a video monitor and a light generator, the light generator often being associated with the video processor of the videoendoscope in the same box.

Fibrescope or videoendoscope type flexible endoscopic probes concerned by this invention and that will be used particularly for medical applications such as bronchoscopy, also have an operating channel composed of a flexible cylindrical pipe that passes firstly in the articulated tip deflection, in the flexible cylindrical duct, then in the distal part of the control handle of the endoscopic probes. The operating channel, the distal end of which is located on the distal face of the distal end piece of the endoscopic probes, is used to carry out all or some of the following operations:

introduction of a flexible instrument such as a clamp, an electrical surgical knife, or laser fiber, that the user can use to take physical action on the target located in front of the distal objective of the flexible endoscopic probe;

suction of tissue debris at the target generated by the work done above;

distribution of a liquid medicine product at the target.

These various operations can only be implemented if an operating device comprising the following elements is integrated into flexible endoscopic probes intended for this type of applications:

the flexible operating channel mentioned above;

a suction input fixed to the control handle and that will be connected to a suction pump through an external flexible pipe;

a control valve usually fixed to the control handle to enable the user to connect a suction input to the proximal end of the operating channel;

an instrument input fixed to the control handle and directly connected to the proximal end of the operating channel, the instrument input usually being provided with a removable silicone cap to seal the input and also to enable entry of a flexible instrument or the conical end piece of a syringe containing a product that will be injected into the operating channel.

The architecture of the operating device of flexible endoscopic probes that enable use of the above mentioned operations must satisfy ergonomic constraints and disinfection constraints at the same time.

Ergonomic constraints relate to access to functions for "suction control" and for the introduction of instrument(s) that must be located on the control handle so as to facilitate the operator's work.

Disinfection constraints apply equally well to fixed elements in the operating device integrated into the endoscopic probe, and removable elements external to said device. Said removable elements such as the suction control valve and the sealing cap, must be either disposable, or they must be removable so that they can be cleaned by brushing before being disinfected by immersion in a disinfecting bath, or even better by putting into the autoclave. It must be easy to clean fixed elements in the operating device such as the operating channel and the various connecting pipes rigidly fixed into the control handle, using cylindrical brushes before the endoscopic probe is fully immersed in a disinfection bath.

Flexible endoscopic probes for medical purposes enabling use of a suction control and an instrumentation input, in practice are based on two types of architecture.

The first architecture routinely used in flexible endoscopic probes enabling use of a suction control and an instrumentation input concerns probes like that shown in FIG. 1, in which the control handle 1 comprises two distinct accesses 41 and 45 to the operating channel 9 connected through a tubing 12, 13 integrated into the handle 1. The first of these accesses 41, located at the distal end of the control handle 1, applies to the instrument input. The second access 45, located at the proximal part of the handle 1, is fitted with a removable external suction assembly F, and includes the suction control 30 and a suction tubing 10 comprising a connection end piece to an external suction pump. This type of operating device was described by the Japanese Company OLYMPUS in U.S. Pat. No. 5,299,561 and U.S. Pat. No. 5,840,015. Another operating device of the same type was described by the Japanese Company OLYMPUS in U.S. Pat. No. 5,257,773 and U.S. Pat. No. 5,322,263. This type of device has also been used in fibrescopes in the FB series and videoendoscopes in the EB series made by the Japanese Company PENTAX, and fibrescopes in the 40 and 160 series made by the Japanese Company OLYMPUS. The implantation of the instrument input 41 and the suction control 30 of the suction device F at the ends of the control handle 1 of the flexible endoscopic probes based on this type of architecture, has an undeniable advantage in terms of ergonomy.

It is more ergonomic to use one hand to hold the handle 1 of the probe and possibly manipulate the suction control 30 of the suction assembly F, and to use the other hand to manipulate the operating instrument inserted into the instrument input 41 that is not close to the suction control 30.

However, integration of an internal tubing 12 and 13 into the control handle 1 to connect two inputs 41 and 45 to the operating channel 9 is undoubtedly a handicap in terms of ease of cleaning and disinfection.

It is very difficult, if not impossible, to disassemble this internal tubing 12, 13 from the handle to clean it. In this case, cleaning is usually done inside the control handle at the risk of leaving impurities in the Y branch formed by tubings 13, 12, 9, a location at which tissue debris are particularly likely to collect.

The second of these architectures concerns endoscopic probes like that described in FIG. 2, in which the control handle is provided with a single unique access to the operating channel, this access being equipped with an external operating device E1, that may be fully or partially removable depending on the models, and including the instrument input, the suction control and the connection end piece to an external suction pump. This type of operating device was described by the Japanese Company OLYMPUS in U.S. Pat. No. 4,198,958, U.S. Pat. No. 4,469,090 and U.S. Pat. No. 4,561,428. Another operating device of this type was described by the Japanese Company OLYMPUS in U.S. Pat. No. 4,736,732 and U.S. Pat. No. 4,794,913. This type of device has also been used in bronchoscopes in the FBS series made by the Japanese Company MACHIDA and in bronchoscopes in the 20 series made by the Japanese Company OLYMPUS.

Direct access to the operating channel that characterizes flexible endoscopic probes based on this type of architecture has an undeniable advantage in terms of the ease of cleaning and disinfection, since the external operating device can easily be disassembled from the handle of the endoscope.

However, this single piece removable operating device E1 is not very ergonomic to use, due to the proximity of the instrument input and the suction control.

SUMMARY OF THE INVENTION

The purpose of this invention is to make a removable operating device for a flexible endoscopic probe with a preferably medical purpose and provided with a single unique access to the operating channel 9, this operating device needing to be easily removable, ergonomic to manipulate and it should satisfy disinfection constraints required by users.

This objective is achieved by providing an operating device designed to be removably fixed onto an endoscopic probe handle including an internal operating channel having an input opening up in a distal part of the handle, said operating device comprising:

a means for inserting operating instruments, including an instrument insertion conduit having a distal end which comprises means for connecting the instrument insertion conduit to the operating channel input, and a proximal end which forms an instrument input for the operating device, and a suction assembly comprising a suction conduit communicating with the insertion conduit and a control means for selectively connecting the suction conduit to a pump, to suck out fluids through the operating channel.

According to the invention, this operating device comprises a connecting conduit putting the suction conduit into communication with the insertion conduit, and having a length such that when the operating device is fixed on an endoscopic probe handle, the suction control means is positioned close to the control means of said handle located in a proximal position of said handle.

This operating device is then removable from the endoscope handle 1, for example so that it can be sterilized, and is also ergonomic to use since the suction control 30 is sufficiently close to the control means of the endoscope so that it can be manipulated with the same hand as the endoscope control means.

Advantageously, the length of the connecting conduit is of the order of the thickness of several fingers of a hand.

Preferably, the connection means of the insertion conduit are designed so as to removably fix the operating device on the handle.

According to one embodiment of the invention, this operating device comprises an additional attachment means located at the suction assembly, designed to cooperate with complementary attachment means provided on the proximal part of the handle.

The connecting conduit 16 is preferably made of a rigid material.

According to another embodiment of the invention, the suction control means is a removable valve that can adopt at least one open configuration enabling fluid to pass between the operating channel and a suction tubing itself connected to the suction pump, and a closed configuration preventing passage of the fluid to the suction tubing.

According to another embodiment of the invention, the suction assembly comprises a cylindrical part installed so as to slide freely inside the suction conduit, and comprising a closed axial channel and a lateral orifice connecting the outside of the cylindrical part to the inside of the closed axial cylindrical channel, the cylindrical part closing the inlet to the suction tubing in the closed configuration, the side orifice being in the open configuration facing the suction tubing inlet.

Preferably, the cylindrical part is pushed into the closed configuration by elastic return means.

According to another embodiment of the invention, the suction conduit of the suction assembly is selectively connected by the control means to an injection tubing used for selective injection of fluids from the injection tubing to the operating channel.

Advantageously, the means for inserting operating instruments is provided with a cap for closing off the insertion conduit.

Preferably, this operating device is essentially made from a sterilisable material intended for medical purpose, such as stainless steel.

Advantageously, this operating device is made so that it should be disposable.

The invention also relates to a fibrescope and a videoendoscope equipped with the operating device defined above.

One preferred embodiment of the invention will be described below, as a non-limitative example, with reference to the appended drawings.

DETAILED DESCRIPTION

Figure 1:
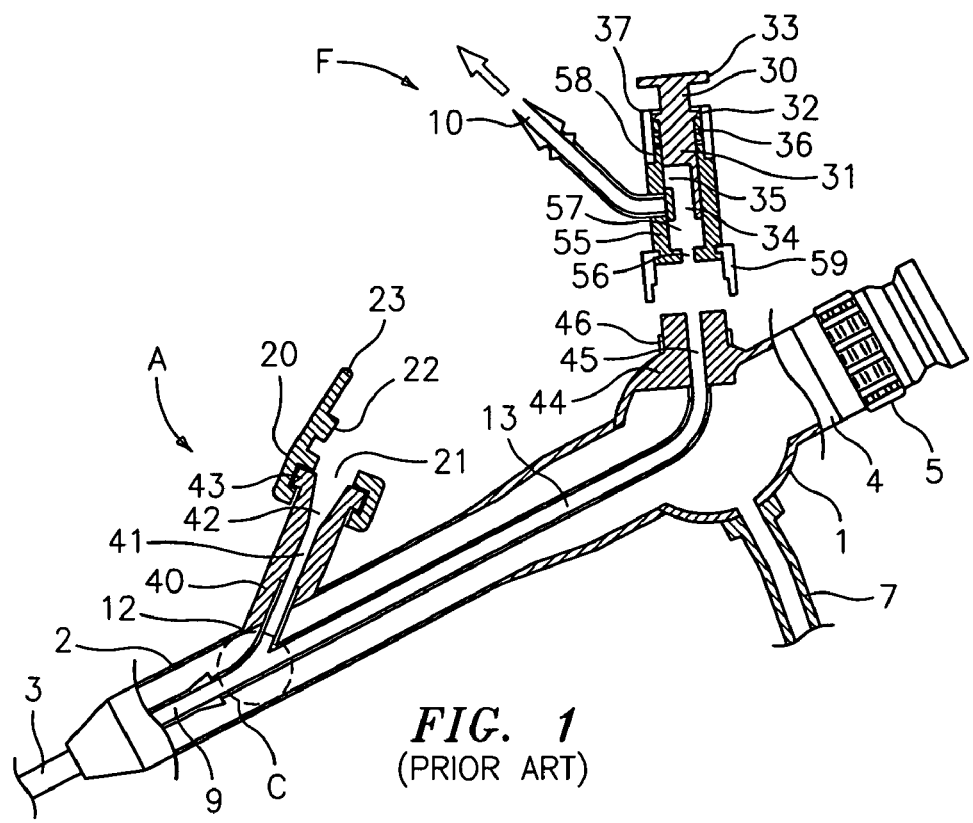
FIG. 1, briefly mentioned above, is a cross-sectional view of an endoscope handle and its partially removable operating device according to prior art.

FIG. 1 illustrates a control handle 1 of a fibrescope according to prior art designed for medical purposes, provided with two distinct accesses 41 and 45 to the operating channel 9 and an external operating device also representative of prior art in this subject.

Like all flexible endoscopic probes designed for medical purposes and equipped with an operating channel, this fibrescope is provided with a control handle 1 fixed to the distal end of a flexible umbilical cable 7 and the proximal end of a flexible duct 3 used particularly for housing the flexible operating channel 9, the proximal end of which opens up into the distal part 2 of the control handle 1.

The various devices commonly integrated into this fibrescope are well known to those skilled in the art, and have deliberately not been shown in FIG. 1 for reasons of clarity. These elements are integrated into the distal part of the flexible duct 3 (objective, illumination window, output from the operating channel, articulated tip deflection, etc.), in the flexible duct 3 (lighting fiber harness, ordered image fibers harness, tip deflection control cables, etc.), in the control handle 1 (tip deflection control device, etc.), in the proximal part 4 of the handle (ocular lens, dioptric adjustment device controlled by the ring 5, etc.), in the flexible umbilical cable 7 (lighting fibers harness, etc.) and in the proximal end of the umbilical cable (connection end piece to a light generator, etc.).

The distal part 2 of the control handle 1 of the fibrescope illustrated in FIG. 1 is provided with a first oblique lateral socket 40 in which a cylindrical channel 41 is formed in which the conical shaped proximal end 42 forms the instrumentation input to the fibrescope and in which the distal end C is connected to the proximal end of the operating channel 9 through a rigid cylindrical tubing 12 fixed housed in the distal part 2 of the control handle. The proximal end of the socket 40 is provided with an external shoulder 43 used to put a sealing cap 20 made of a flexible plastic material into position. The cap is provided with a circular crossing orifice 21 that can be closed off by a cylindrical shutter 22 fixed to a sealing cover 23 elastically connected to the cap.

The control handle 1 of the fibrescope illustrated in FIG. 1 is also provided with a second lateral socket 44 in which a cylindrical channel 45 is formed, with its proximal end forming the suction input of the fibrescope to which the suction assembly F is connected, and the distal end of which is connected to the distal end of the tubing 12 through a rigid cylindrical tubing 13 housed fixed in the distal part 2 of the control handle. The proximal part of the socket 44 is provided with an external thread 46 intended to connect the suction assembly F of a removable external operating device.

Therefore, the operating device comprises a suction assembly F comprising a tube 55, the distal end of which is provided with an axial circular orifice 56, and the proximal part of which contains an axial cylindrical channel 57. The tube 55 of the suction assembly F is fixed to a rigid lateral suction tubing 10, the distal end of which opens up into the cylindrical channel 57 also called the suction conduit. The distal end of the tube 55 is fixed to a loose ring 59, the distal part of which is provided with an internal thread used to fix the operating device onto the control handle 1 by screwing the ring onto the external thread 46 formed around the second socket 44. The proximal part of the tube 55 is provided with an external thread 58 used to fix the valve mechanism 30 described below onto said tube.

This removable valve mechanism 30 consists of a cylindrical part 31 housed free to slide in the suction conduit 57 formed in the proximal part of the tube 55 of the operating device. The distal part of the cylindrical part 31 is provided with a closed axial channel 34 which is generally cylindrical, and a lateral circular orifice 35 opening up into the proximal end of the closed channel 34. The proximal part of the cylindrical part 31 is provided with a proximal end 33 in the form of a push button, an external cylindrical shoulder 32 and a loose ring 37, the proximal edge of which rests on the proximal face of the shoulder 32 and the distal part of which is provided with an internal thread to screw the ring 37 onto the external thread 46 formed around the proximal part of the tube 55 of the operating device. A helical spring 36 housed between the proximal edge of the tube 55 and the distal face of the shoulder 32 holds the valve mechanism 30 in a rest position characterized by closing the distal end of the suction tube 10. Manual action on the proximal end 33 of the valve mechanism brings the lateral orifice 35 facing the distal end of the suction tube 10, so that the suction tube 10 can be connected to channel 45 formed in the socket 44.

Figure 2:
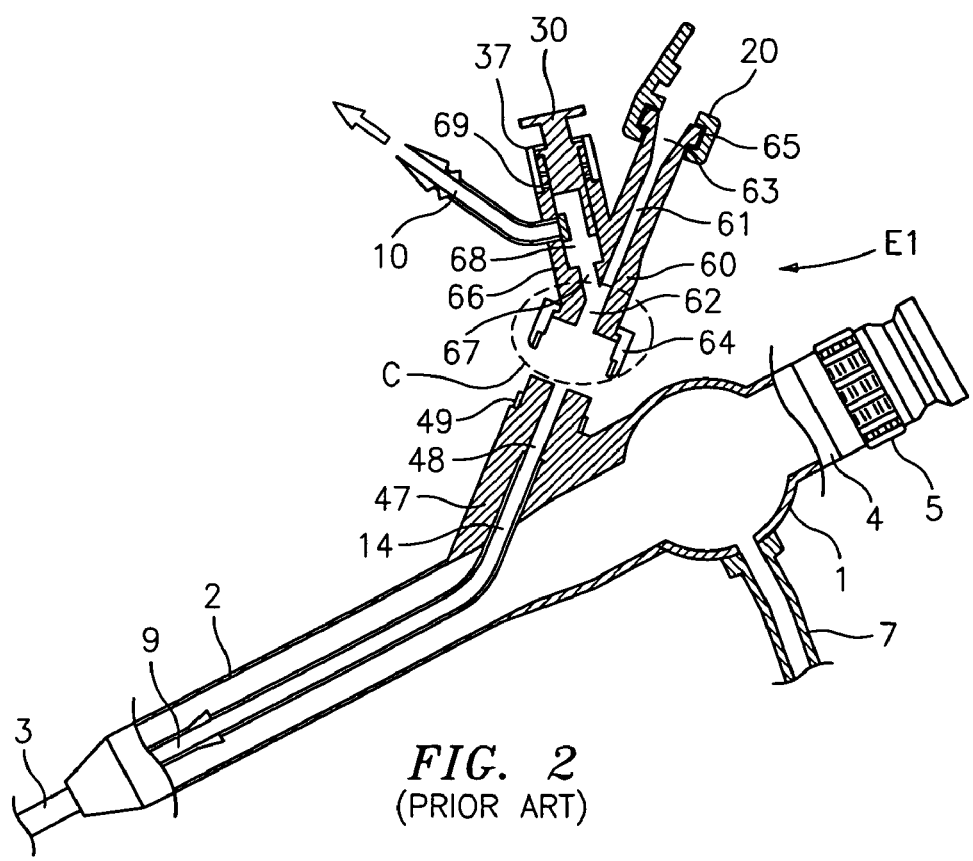
FIG. 2, briefly described above, is a cross-sectional view of an endoscope handle and its completely removable operating device according to prior art.

FIG. 2 illustrates the structure of a handle 1 of a fibrescope used for medical purposes provided with a single and unique access 48 to the operating channel 9 in the proximal position, and an external operating device E1 representing prior art in the subject.

Like all flexible endoscopic probes for medical purposes equipped with an operating channel 9, this fibrescope is provided with a control handle 1 fixed to the distal end of a flexible umbilical cable 7 and the proximal end of a flexible duct 3 used particularly for housing the flexible operating channel 9, the proximal end of which opens up into the distal part 2 of the control handle 1.

The various devices usually integrated into this fibrescope are well known to those skilled in the art and are deliberately not shown in FIG. 2, for reasons of clarity. These elements are integrated into the distal part of the flexible duct 3 (objective, illumination window, output from the operating channel, articulated tip deflection, etc.), in the flexible duct 3 (lighting fiber harness, ordered image fibers harness, tip deflection control cables, etc.), in the control handle 1 (tip deflection control device, etc.), in the proximal part 4 of the handle (ocular lens, dioptric adjustment device controlled by the ring 5, etc.), in the flexible umbilical cable 7 (lighting fibers harness, etc.) and in the proximal end of the umbilical cable (connection end piece to a light generator, etc.).

The control handle 1 of the fibrescope illustrated in FIG. 2 is provided with an oblique lateral socket 47 in which a cylindrical channel 48 is formed, the distal end of which is connected to the proximal end of the operating channel 9 through a rigid cylindrical tubing 14 housed in the distal part 2 of the control handle. The proximal part of the socket 47 is provided with an external thread 49 that will be used for connection of an external operating device E1.

The operating device E1 is in the shape of a Y, in which the main branch is located along the prolongation of the line of the socket 47 and contains the instrumentation channel, and the oblique lateral branch contains the suction channel. The main branch of the operating device E1 comprises a tube 60 in which a cylindrical channel 61 is formed with its conically shaped proximal end 63 forming the instrumentation input. The proximal end 63 of the tube 60 is provided with an external shoulder 65 used to put the sealing cap 20 described above with reference to FIG. 1 into position. The distal end of the tube 60 is fixed to a loose ring 64, the distal part of which is provided with an internal thread used to fix the operating device E1 onto the control handle 1 by screwing the ring 64 onto the external thread 46 formed around the socket 47. The oblique lateral branch of the operating device E1 consists of a tube 66 rigidly fixed to the tube 60; and the distal end of which contains an axial channel 67 opening up into the distal end 62 of the channel 61 formed in the tube 60. The proximal part of the tube 66 is provided with an external thread 69 used to screw the ring 37 of the cap mechanism 30 described above with reference to FIG. 1, and previously inserted into the cylindrical channel 68 formed in said proximal part, onto the tube. The tube 66 is also fixed to a rigid lateral suction tubing 10, for which the distal end opens up into the cylindrical channel 68.

Figure 3:
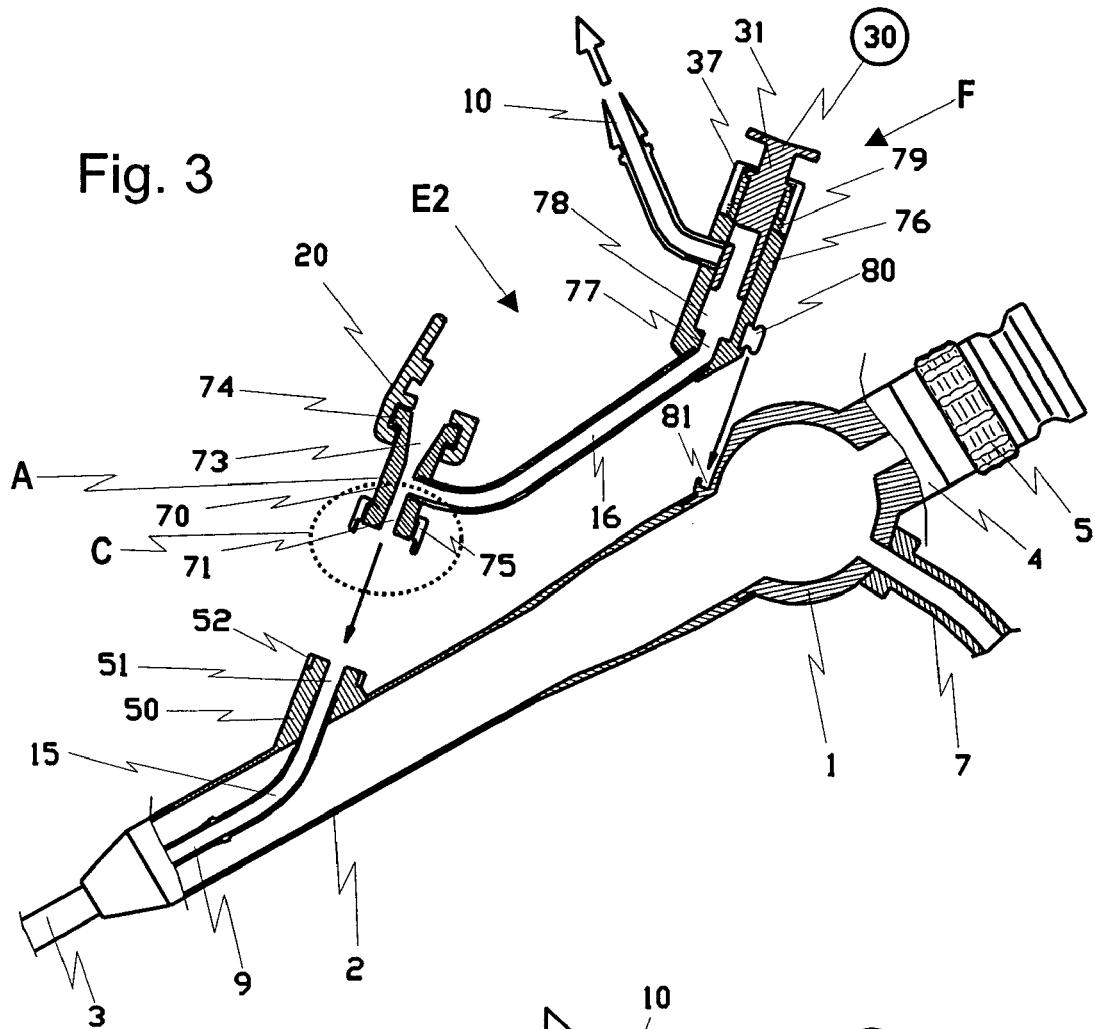
FIG. 3 is a cross-sectional view of an endoscope handle and an operating device according to the invention.

FIG. 3 illustrates the structure of a fibrescope for medical purposes provided with a single and unique access 51 to the operating channel 9 and provided with an external operating device according to this invention.

Like all flexible endoscopic probes for medical purposes equipped with an operating channel, this fibrescope is provided with a control handle 1 fixed to the distal end of a flexible umbilical cable 7 and the proximal end of a flexible duct 3 used particularly for housing the flexible operating channel 9, the proximal end of which opens up in the distal part 2 of the control handle 1.

The various devices usually integrated into this fibrescope are well known to those skilled in the art and are deliberately not shown in FIG. 3, for reasons of clarity. These elements are integrated into the distal part of the flexible duct 3 (objective, illumination window, output from the operating channel, articulated tip deflection, etc.), in the flexible duct 3 (lighting fiber harness, ordered image fibers harness, tip deflection control cables, etc.), in the control handle 1 (tip deflection control device, etc.), in the proximal part 4 of the handle (ocular lens, dioptric adjustment device controlled by the ring 5, etc.), in the flexible umbilical cable 7 (lighting fibers harness, etc.) and in the proximal end of the umbilical cable (connection end piece to a light generator, etc.).

The distal part 2 of the control handle 1 of the fibrescope illustrated in FIG. 3 is provided with an oblique lateral socket 50 in which a cylindrical axial channel 51 is formed, the distal end of which is connected to the proximal end of the operating channel 9 through a rigid cylindrical tubing 15 fixed housed in the distal part 2 of the control handle. The proximal part of the socket 50 is provided with an external thread 52 that will be used to connect the external operating device E2 according to this invention.

The distal part of the operating device E2 comprises a means of insertion A composed of a cylindrical part 70 in which an instrument insertion conduit 71 is formed, the flared proximal end 73 of which forms the instrument input. The proximal end 73 of the cylindrical part 70 is provided with an external shoulder 74 used to put the sealing cap 20 described above with reference to FIG. 1, into place. The cylindrical part 70 is also rigidly fixed to a rigid lateral connecting conduit 16, for which the distal end opens up in the instrument insertion conduit 71. The distal end C of the cylindrical part 70 of the insertion means A is fixed to a loose ring 75, for which the distal part is provided with an internal thread used to fix the operating device E2 onto the distal part 2 of the control handle 1 by screwing the loose ring 75 onto the external thread 52 formed around the proximal part of the socket 50.

The proximal part of the operating device E2 is formed from a tube 76, the distal end of which is provided with a circular orifice 77 in which the proximal end of the rigid connecting conduit 16 is rigidly housed. The proximal part of the tube 76 is provided with an external thread 79 used to screw the ring 37 of the valve mechanism 30 described above with reference to FIG. 1, after being inserted in the cylindrical suction duct 78 formed in the proximal part, onto said tube. The tube 76 is also rigidly fixed to a rigid lateral suction tubing 10, the distal end of which opens up into the cylindrically shaped suction conduit 78. The distal part of the tube 76 is provided with an external lateral pin 80 provided with a shoulder that is inserted into a slit formed on the control handle 1 for this purpose, to fix the distal part of the operating device E2 and the control handle 1.

Figure 4:
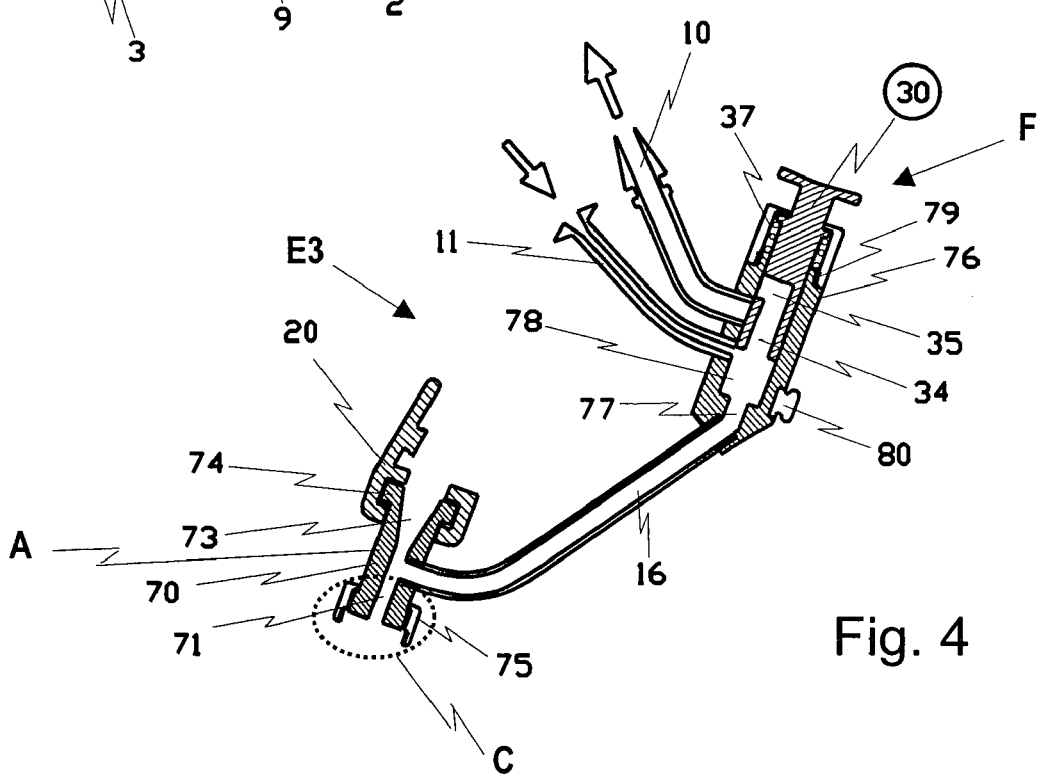
FIG. 4 is a cross-sectional view of a variant of the operating device according to the invention, shown in FIG. 3.

FIG. 4 illustrates another version of the operating device E3 according to this invention, used in cooperation with the same valve mechanism to simultaneously manage functions for suction and injection of a liquid contained in a perfusion pack connected to the operating device E3 through a flexible pipe, into the operating channel 9. The use of such of a device in bronchoscopy provides a means of carrying out "alveolar washing" operations.

The operating device E3 illustrated in FIG. 4 is the same as that described with reference to FIG. 3 except that the structure of its proximal part formed by a tube 76 rigidly fixed firstly to a rigid lateral suction tubing 10, the proximal end of which opens up into the proximal part of the suction conduit 78 in the shape of a cylindrical channel, formed in the tube 76, and also a rigid lateral injection tubing 11, the proximal end of which opens up in the suction conduit 78.

When the valve mechanism 30 is at rest, this type of operating device E3 prevents any communication between the suction tube 10 and the connecting conduit 16, and also prevents any communication between the injection tube 11 and the connecting conduit 16.

When the user activates the valve mechanism 30 by sliding the sliding cylindrical part 31 into a first open position, the device enables communication between the suction tube 10 and the connecting conduit 16 and prevents any communication between the liquid injection tube 11 and the connecting conduit 16.

When the user activates the valve mechanism 30 by sliding the sliding cylindrical part 31 into a second open position, the device prevents communication between the suction tube 10 and the connecting conduit 16 and allows communication between the liquid injection tube 11 and the connecting conduit 16.

Therefore, obviously provided that the instrumentation input 73 is closed off by the sealing cap 20, it is observed that this type of operating device E3 effectively enables the user to simultaneously manage fluid suction and/or liquid injection into the operating channel 9, using a single control means 30.

Figure 5:
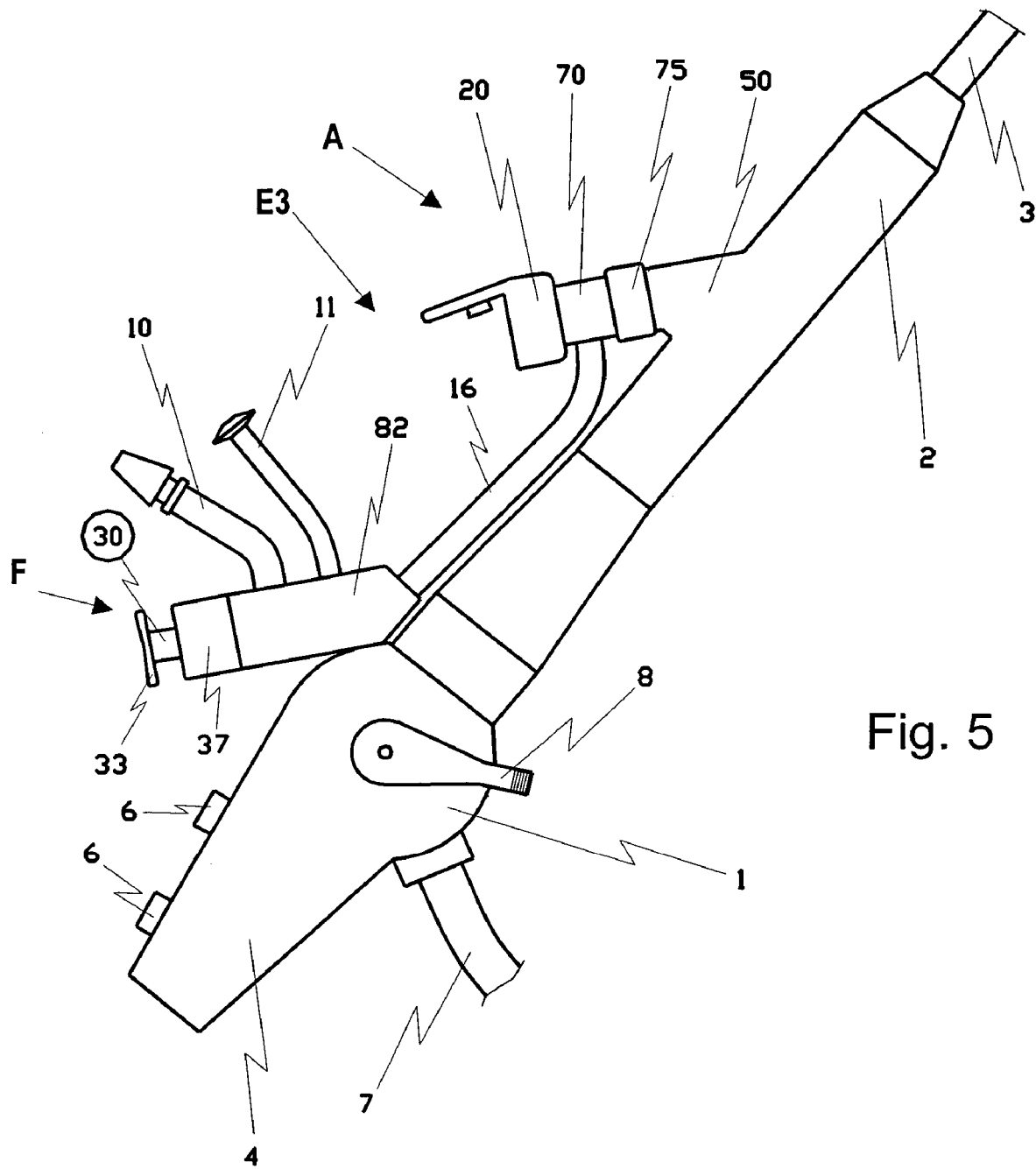
FIG. 5 is a profile view of a control handle for a videoendoscopic probe equipped with the operating device according to the invention.

FIG. 5 illustrates the external appearance of the control handle 1 of a videoendoscopic probe equipped with the operating device E3 described above with reference to FIG. 4.

The distal part 2 of the control handle is provided with a socket 50 housing the access channel to the operating channel and is rigidly fixed to the proximal end of the flexible duct 3 of the videoendoscope, the distal end of this duct containing various elements (such as the articulated tip deflection, illumination window, output from the operating channel, optoelectronic device, etc.) well known to those skilled in the art, and mentioned above. The control handle 1 is fixed to the distal end of an umbilical cable 7, the proximal end of this cable containing various elements (such as the connection end piece to a lighting generator, connector to a video processor, etc.), also well known to specialists in the subject and also mentioned above.

The control handle 1 is provided with a control lever 8 used to control the orientation of the distal tip deflection of the videoendoscopic probe and a proximal part 4 equipped with keys 6 used to remote control some functions of the video processor connected to the proximal end of the umbilical cable 7.

The external operating device E3 described above with reference to FIG. 4 is fixed to the control handle 1 by screwing the loose ring 75 fixed to the distal end 70 of the device onto the socket 50.

The proximal part 82 of the operating device E3 is provided with an air suction inlet 10, a liquid injection inlet 11, and a valve mechanism 30 fixed to the proximal part 32 by screwing the ring 37 fixed to the valve mechanism 30 onto the proximal part.

The connecting conduit 16 connects the distal end 70 of the operating device E3, this distal end being equipped with the sealing ring 20 described above with reference to FIG. 1, to the proximal end 82 of the device.

What is claimed is:

1. An operating device designed to be removably fixed onto an endoscopic probe handle including an internal operating channel, having an input opening up in a distal part of the handle, said operating device comprising:
a means for inserting operating instruments, including an instrument insertion conduit having a distal end comprising means for connecting the instrument insertion conduit to the operating channel input, and a proximal end which forms an instrument input for the operating device, and
a suction assembly comprising a suction conduit communicating with the insertion conduit and a control means for selectively connecting the suction conduit to a pump, to suck out fluids through the operating channel,
a connecting conduit putting the suction conduit into communication with the insertion conduit, the connecting conduit having a length such that when the operating device is fixed on an endoscopic probe handle, the suction control means is positioned close to the control means of said handle located in a proximal part of said handle, and
an additional attachment means located at the suction assembly and designed to cooperate with complementary attachment means provided on the proximal part of the handle.

2. The operating device according to claim 1, wherein the length of the connecting conduit is of the order of the thickness of at least two fingers of a hand.

3. The operating device according to claim 1, wherein the connection means of the insertion conduit are designed so as to removably fix the operating device on the handle.

4. The operating device according to claim 1, wherein the connecting conduit is made of a rigid material.

5. The operating device according to claim 1, wherein the suction control means is a removable valve that can adopt at least one open configuration enabling a fluid to pass between the operating channel and a suction tubing itself connected to a suction pump, and a closed configuration preventing passage of said fluid to the suction tubing.

6. The operating device according to claim 5, wherein the suction assembly comprises a cylindrical part installed so as to slide freely inside the suction conduit, and comprising a closed axial channel and a lateral orifice connecting the outside of the cylindrical part to the inside of the closed axial cylindrical channel, the cylindrical part closing an inlet to the suction tubing in the closed configuration, a side orifice in the open configuration facing the suction tubing inlet.

7. The operating device according to claim 6, wherein the cylindrical part is pushed into the closed configuration by elastic return means.

8. The operating device according to claim 1, wherein the suction conduit of the suction assembly is selectively connected by the control means to an injection tubing used for selective injection of fluids from the injection tubing to the operating channel.

9. The operating device according to claim 1, wherein the means for inserting operating instruments is provided with a cap for closing off the insertion conduit.

10. The operating device according to claim 1, wherein it is made from a sterilisable material intended for a medical purpose.

11. The operating device according to claim 10, wherein said sterilisable material is stainless steel.

12. The operating device according to claim 1, wherein it is made to be disposable.

13. A fiberscope equipped with the operating device according to any one of claims 1 to 3 and 4 to 12.

14. A videoendoscope equipped with the operating device according to any one of claims 1 to 3 and 4 to 12.

* * * * *